United States Patent [19]
Durante et al.

[11] Patent Number: 5,132,472
[45] Date of Patent: Jul. 21, 1992

[54] CATALYTIC OXIDATION OF ALKANES

[75] Inventors: Vincent A. Durante, West Chester; Darrell W. Walker, Media; Steven M. Gussow; James E. Lyons, both of Wallingford; Robert C. Hayes, Media, all of Pa.

[73] Assignee: Sun Refining and Marketing Company, Philadelphia, Pa.

[21] Appl. No.: 599,185

[22] Filed: Oct. 17, 1990

[51] Int. Cl.$^5$ .................. C07C 29/50; C07C 31/04; C07C 2/00

[52] U.S. Cl. .................. 568/910; 568/398.8; 568/399; 568/469.9; 568/475; 568/836; 568/840; 568/910.5; 585/700

[58] Field of Search .................. 568/910.5, 910, 836, 568/840, 469.9, 398.8, 475

[56] References Cited

U.S. PATENT DOCUMENTS

| | | | |
|---|---|---|---|
| 4,618,732 | 10/1986 | Gesser et al. | 568/910 |
| 4,918,249 | 4/1990 | Durante et al. | 568/910 |

FOREIGN PATENT DOCUMENTS

| | | | |
|---|---|---|---|
| 8202548 | 5/1982 | World Int. Prop. O. | 568/910.5 |

Primary Examiner—Marianne Cintins
Assistant Examiner—R. Cook
Attorney, Agent, or Firm—Q. Todd Dickinson; Donald R. Johnson

[57] ABSTRACT

Process is provided for oxidation of organic compounds in which a reaction zone is provided, containing an open space and a bed of solid granular catalyst, an organic feedstock and oxygen are passed in gas phase through the open space and then into contact with the catalyst bed, and reaction products are removed from the open space after relatively less contact with the catalyst, and from at least one other location after relatively greater contact with the catalyst. Greater yield of desired product may be obtained in such operation than in operation where all of the reaction products are removed after the greater contact with the catalyst.

9 Claims, 2 Drawing Sheets

CATALYTIC OXIDATION OF ALKANES

BACKGROUND OF THE INVENTION

In U.S. Pat. No. 4,918,249, issued Apr. 17, 1990, from application Ser. No. 338,916 filed Apr. 17, 1989, a process is disclosed and claimed wherein a feedstock comprising hydrocarbon or an oxygenated hydrocarbon having 1 to 10 carbon atoms is contacted at a temperature of about 350° to 550° C. with air or oxygen and in the presence of a catalytically effective amount of a catalyst containing crystalline silicometallate having iron incorporated in the structural framework.

SUMMARY OF THE INVENTION

This invention is in part an improvement over the process disclosed in said patent, in which improvement feedstock in vapor phase is passed through a bed of solid granular catalyst in a reactor, i.e., reaction zone, and products of oxidation are removed from the reactor at two or more locations corresponding to different average residence times over the catalyst. Superior results with respect to yield of and/or selectivity for desired reaction products, for example methanol from methane and air feedstock, are obtained by the process of the invention, as compared for example with otherwise similar operation in which products of oxidation are removed from the reaction zone at only one location, as in typical operation wherein feedstock is passed through a bed of granular solid catalyst.

DETAILED DESCRIPTION OF THE INVENTION

Figure 1:
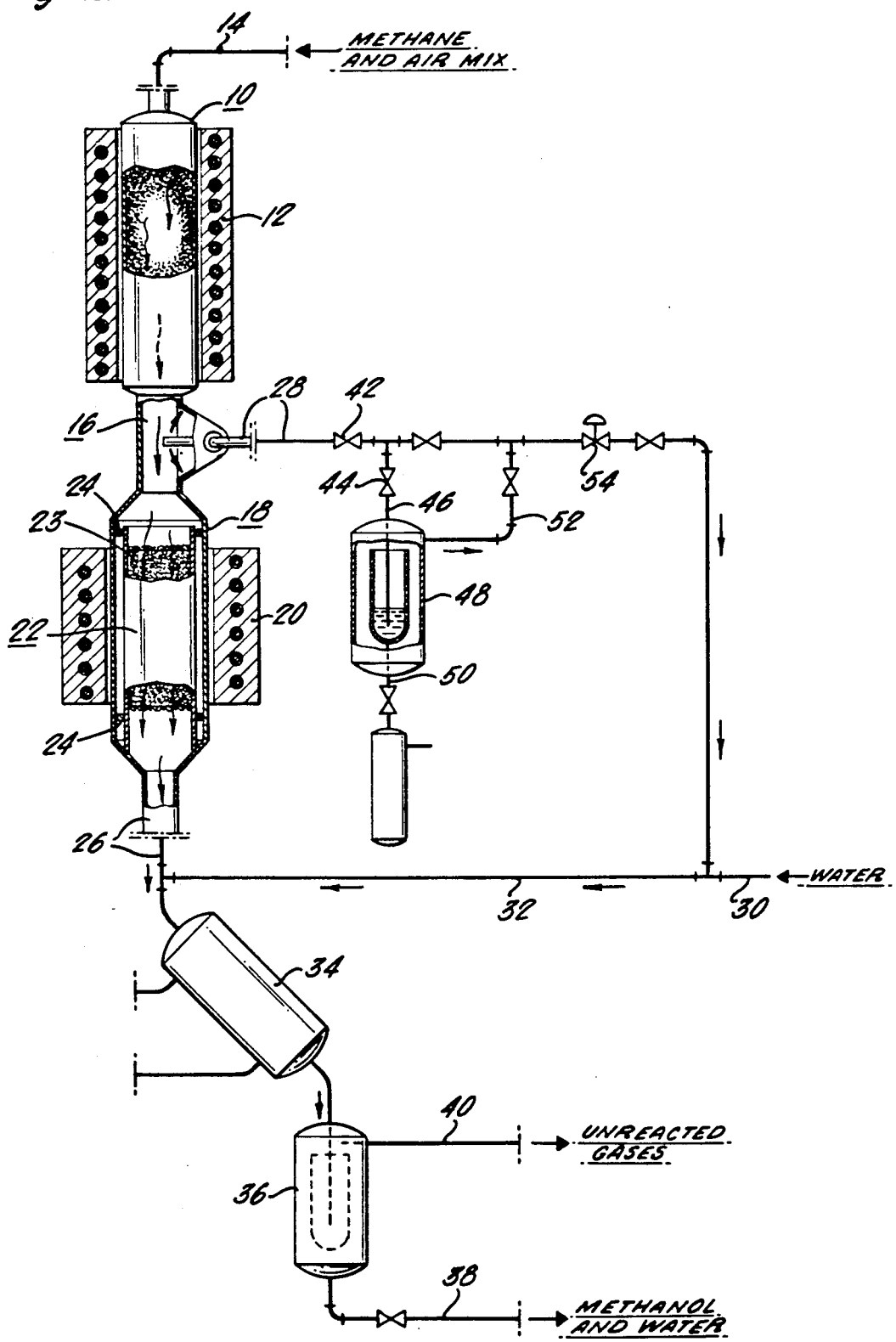

The catalyst which is used in the process according to the invention is a catalyst which is capable of catalyzing oxidation of the feedstock, and the temperature and other conditions employed are those which are effective for oxidation of the feedstock with the catalyst employed.

In one embodiment, the invention involves the provision of a reaction zone containing a bed of granular catalyst and an open space free of catalyst, the introduction of reactants into the open space, passage of reactants from the open space into the catalyst bed, and the withdrawal of reaction products from at least two locations i.e., outlets, in the reactor. From one of the reactor outlets, gases are withdrawn which have had relatively less contact with the catalyst, and from the other outlet gases are withdrawn which have had relatively more contact with the catalyst. It is believed that the enhanced selectivity of this process results from minimizing contact between products and intermediate with the catalyst bed, which contact would result in the formulation of unwanted products. It has been found that a greater yield of desired product is obtained in this operation than in operation in which products are withdrawn from either outlet alone, even the outlet for the gases that have had relatively more contact with the catalyst.

According to one embodiment of the invention, one outlet samples the open space above the catalyst bed and the other outlet samples effluent from the bottom of the bed. In another embodiment, using a more highly backmixed reactor, reactant gases are mechanically impelled from at least a portion of the open space into the catalyst bed, and reaction products are withdrawn from two locations, one distant from and one proximal to the fixed catalyst bed. The distant location is in the open space whereas the proximal location can be below the catalyst bed or even be within the catalyst bed, the important aspect being that the two locations represent different average residence times.

In a particular embodiment, the direction of flow of gases is downward and products are withdrawn from a location adjacent and above the top of the catalyst bed as well as from the bottom of the catalyst bed. Without limiting the invention to any theory, it is believed that reaction occurs at the interface between the top of the catalyst bed and the adjacent open space, or at a location just beneath the interface, and that products or intermediates migrate to the open space where they undergo additional reaction, among themselves and/or with additional feed, to form products, and are withdrawn therefrom.

In another embodiment, the direction of flow of gases into the catalyst bed is horizontal. Reactant gases flow into a central open space surrounded by an annular catalyst bed, and are impelled horizontally into contact with the catalyst bed. Products produced by reaction in the bed pass from the catalyst bed into the open space again. Products are withdrawn from upper and lower locations in the reaction zone, the products withdrawn from the lower location having had a larger average contact time with the catalyst than the products withdrawn from the upper location.

In most applications of the process, the volume of the open space portion of the reaction zone will be 0.5-10 times that of the catalyst bed. The reaction zone will usually be adiabatic with the average temperature of the catalyst bed being different (usually higher) than that of the open space. There will also usually be a temperature gradient within the open space.

Another embodiment of the invention is based on the proffered explanation above that intermediates migrate to the open space where they undergo additional reaction with feed, i.e., reactant material, to form more product. This embodiment is based on the finding that in a once-through operation, e.g., where feed is introduced into the top of the catalyst bed and product is removed from the bottom, the removed product often contains intermediates as well. If this intermediate-containing product is mixed with more feed material, the intermediates and feed react to form more product. It should be pointed out that feed should be introduced into these effluent intermediates very soon after withdrawing the intermediates, so that they do not have time to react among themselves or with effluent product to form something else.

The reaction is preferably carried out in an adiabatic reactor. There will usually be a temperature gradient in the open space from the point of entry of the feed to the catalyst bed and, in addition, the average open space temperature will usually differ (be lower) than that of the catalyst bed. The open space volume will usually be 0.5-10 times the catalyst bed volume.

Preferred catalysts used according to the invention are those disclosed in said U.S. Pat. No. 4,918,249. These catalysts contain crystalline silicometallates or zeolites with both iron and silicon incorporated in the structural framework. Additional iron which is not part of the zeolitic framework may also be present. Other metals may also be present, either in the framework, as exchangeable ions, or as occluded species which are neither exchanged nor part of the framework. These species in addition to iron and silicon may exist as neutral monometallic compounds or as oligomers; they may or may not be crystalline. Examples of elements which may be present as ions, as neutral monomeric compounds, or as oligomers in addition to iron and silicon are Cr, V, Co, Mo, Mn, Ru, Pt, U, Sn, Sb, Bi, Te, Al, B, Ga, Ge, Zr, Ti, P, S. Binders may also be added to the catalyst composition.

An example of a material which may be used as a catalyst in the process according to the invention is the ferrisilicate (silicoferrate) analog of sodalite as disclosed by Szostak and Thomas in *Chem. Commun.*, 1986, page 113, prepared by adding short-polymeric-unit aqueous sodium metasilicate to aqueous iron nitrate, acidifying to form a gel, adding tetramethylammonium chloride to the gel and heating in an autoclave to provide a white powder with an x-ray pattern characteristic of the cubic sodalite structure. Ferrisilicate analogs of ZSM-5 and mordenite have also been disclosed in references cited by Szostak et al supra.

In Szostak, "Molecular Sieves, Principles of Synthesis and Identification," Van Nostrand Reinhold Catalysis Series, Van Nostrand Reinhold, N.Y. 1989, in Table 4.1 on pages 209-210, various metallosilicate molecular sieves containing iron in ZSM-5, levynite, and mordenite structures are disclosed as having been patented; on page 232, referring to work of Iton et al, ferrialuminosilicate analogs of the zeolite ZSM-5 with a reported x-band in the e.s.r. at 4.28, consistent with the presence of some structural iron, is disclosed, the focus of this work being on preparing a shape-selective iron-containing molecular sieve for use as a Fisher-Tropsch catalyst, activity for the latter being related to the presence of non-framework iron; on page 233, referring to work of Calis et al, preparation of ferrisilicate molecular sieves using a published method for preparing zeolite ZSM-5, except for replacing the aluminum source with ferric nitrate, is disclosed; on page 237, it is disclosed that iron is thermally less stable in the silicate framework than aluminum; on page 238, it is disclosed that the Mossbauer spectrum of ferrisilicate with the ZSM-5 structure and $SiO_2/Fe_2O_3$ of 98 indicate extremely high dispersions of octahedral iron oxide in the material, this highly dispersed nonframework iron having been found to contribute significantly to the catalytic activity of the bulk material.

According to one embodiment of preferred catalysts for use in the present invention, silicometallates containing iron in at least a portion of the structural framework are employed as catalysts. Aluminum, gallium, germanium, boron, phosphorus, vanadium and the like may optionally also be present as framework elements of the crystalline structures so long as iron and silicon are also present. If the predominant tetrahedral atom is silicon and the non-silicon framework metal ions or complexes are of formal charge or valence other than +4, then ion exchange capacity may develop in the structure. Exchange ions may then also be present. If the frameworks are negatively charged due to isomorphous substitution for silicon of iron or other elements or oxocomplexes of these elements of formal charges less than +4, these exchange ions can be any suitable cations including but not limited to $H+$, $Na+$, $K+$, $NH_4+$, $NR_4+$ where R is a hydrocarbon radical, $Ca^{2+}$, $Fe^{3+}$, $Fe^{2+}$ and the like or cationic coordination complexes of metals. If the frameworks are positively charged due to substitution of silicon by an iron-containing entity of formal charge greater than +4, then the frameworks may develop anion exchange capacities. Inorganic or organic anionic species can then be incorporated into the active compositions by ion exchange. If the non-silicon framework metal ions or complexes are of formal charge or valence of +4, then the framework is neutral and no ion exchange capacity is developed. Crystallization directing agents commonly known as templating agents such as organic amines or amine cationic species may also be present in the structure after calcination in varying amounts, preferably not exceeding 10 wt. %, more preferably not exceeding 5 wt. %.

The ratio of framework silicon to framework iron in the preferred compositions for use according to the invention is typically in the range from 2 to about 100,000, preferably 2 to about 15. In the case of cationic frameworks such as iron sodalite, the degree of framework incorporation of iron (III) may be estimated from the sodium exchange capacity. For example, in preparation of iron sodalite, where the Fe/Na atomic ratios after washing out excess sodium species and calcining are about 0.8 plus or minus 0.05, it is estimated that about 20 atomic % of the iron is not in the framework but may exist as occluded or ion exchanged moieties in the calcined zeolites.

Sodalite is a preferred framework structure according to the invention, since it is possible to obtain relatively high loadings of iron in sodalite. Preferred structures are those which contain four rings of tetrahedral aroms (Si, Fe, etc.) since these are expected to favor the formation of iron sites relatively close together but not adjacent. Without limitation to a particular theory, the mechanism of catalysis may involve more than one iron site or an iron plus a silicon site acting in concert, so that greater iron loadings provide proximate iron sites with increased catalytic activity.

The preferred catalysts used according to the invention may be made according to known procedures for making silicoferrate catalysts. (Silicoferrates may be referred to in the prior art as ferrisilicates). The procedure may involve the autoclaving of an aqueous solution of a silicate, an iron salt and a template and water washing, drying and calcining the solid product of the autoclaving. The extent of the calcination is controlled to avoid over-calcination, which may be detrimental to the activity of the catalyst, and under-calcination, which also may be detrimental because of leaving too much template in the structure.

The feedstock for the process of the invention is a hydrocarbon or an oxygenated hydrocarbon having 1 to 10 carbon atoms in the molecule. Hydrocarbon feedstocks include aliphatic, aromatic and cycloaliphatic hydrocarbons, such as methane, ethane, ethylene, propane, n-butane, isobutane, butylenes or mixtures of light alkanes such as natural gas or of alkanes and alkenes in naturally occurring compositions or process streams, hexanes, decanes, benzene, toluene, xylene, naphthalene, cyclohexane, methyl cyclohexane, ethyl cyclohexane, tetrahydronaphthalene, decahydronapthalene and the like. Oxygenates such as alcohols, aldehydes, ketones, esters and the like are prevalent among the products of oxidation of such hydrocarbons. Products of oxidative coupling are obtained in some instances, for example 2,3-dimethylbutane as oxidative coupling product of propane. Oxygenated hydrocarbon feedstocks include for example methanol, butanols, acetone and higher ketones, aldehydes, valeric acid, phenol, cyclohexanol and the like. The products of oxidation are the further oxygenated derivatives of such feedstock, by further oxidation of functional groups or oxidation at additional points in a carbon chain or both.

In one embodiment the oxidation is carried out in a packed bed reactor at temperatures between 300° and 600° C. and preferably between 350° and 475° C. at pressures between 1 atmosphere and 100 atmospheres and preferably between 10 and 70 atmospheres, with gas hourly space velocities of from 100 to 30,000 and preferably from 500 to 15,000 $hr^{-1}$ using air or oxygen as the oxidizing gas in combination with the light hydrocarbon. When air is used as the oxidant, hydrocarbon/air ratios of between 0.1 to 10 and preferably 0.5 to 5 are effective. When oxygen is used, hydrocarbon/oxygen ratio can be from 0.5 to 50 and preferably 5 to 25. Some of these ratios are within explosive limits and care should be taken to operate behind barricades or similarly shielded devices when running in the explosive region. Water may optionally be fed to the reactor with the hydrocarbon-oxidant mixture or after the reactor to capture oxygenated products which are formed.

Figure 2:
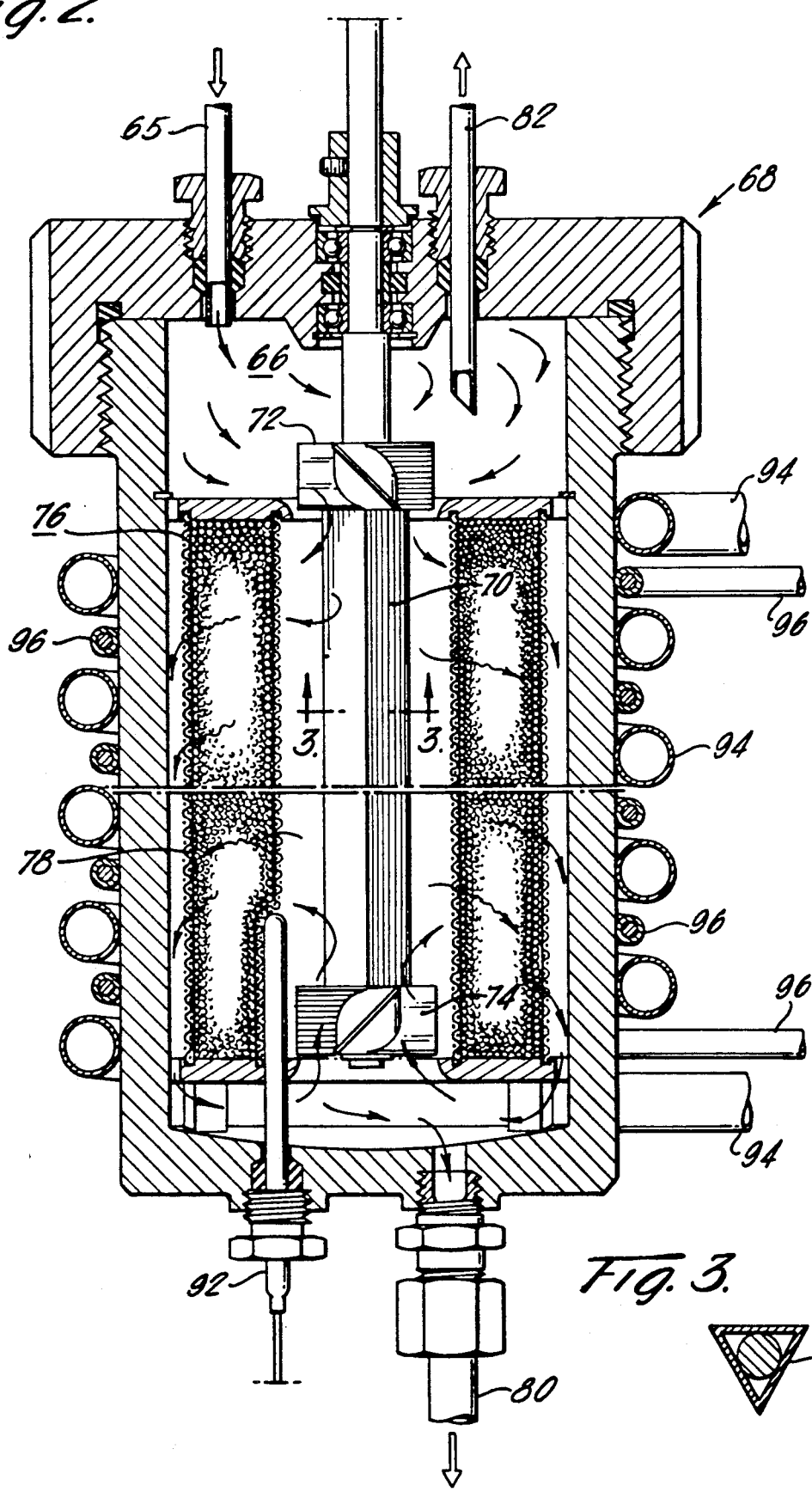
Figure 3:
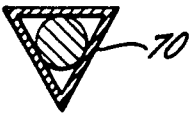

The invention will be further described with reference to the attached drawings in which FIG. 1 illustrates a reaction system including a downflow reactor with an open reaction zone at the top, with a catalyst bed beneath, product being withdrawn from at least two locations spaced along the gaseous flow path, FIG. 2 illustrates a different reactor configuration for a reaction system otherwise similar to that in FIG. 1, and FIG. 3 is a cross-section of the rotor 70 in FIG. 2.

Referring now to FIG. 1, 10 is a preheater filled with glass beads and heated by electrical heater 12. A mixture of methane and air is passed to heater 10 through line 14 and from there into open reaction zone 16 and from there into a quartz-lined stainless steel reactor 18 heated by electrical heater 20. Inside reactor 18 is a quartz liner 22 packed with catalyst 23. The liner 22 is spaced by Teflon O-rings 24 from the wall of reactor 18. Gaseous effluent containing unreacted methane and oxygen and reaction products including methanol is withdrawn from reactor 18 through line 26. A bypass line 28 withdraws gaseous material from open reaction zone 16. Water is introduced through lines 30 and 32 into effluent line 26 to dissolve methanol reaction product and the effluent then goes through condenser 34 and gas liquid separator 36 from which methanol and water are removed through line 38 and unreacted gases through line 40. Valve 42 in line 28 enables gaseous material to be withdrawn through line 28 if desired. Valve 44 enables gaseous material to be withdrawn from line 28 and passed through line 46 into cold trap 48 where methanol is condensed from the gaseous material and removed through line 50. Metering valve 54 enables the rate of flow of gaseous material through line 28 to be regulated. Gaseous material from which methanol has been removed is returned to line 28 through line 52.

Referring now to FIG. 2, a preheated mixture of methane and air is passed into open reaction zone 66 in an upper portion of continuous stirred tank reactor 68 containing triangular-cross-section rotor 70, the cross section of which is shown in FIG. 3, having upper turbine blades 72 and lower turbine blades 74 attached thereto. Inserted in the reactor 68 is an annular screen basket 76 containing solid granular catalyst 78. Basket 76 has feet not shown which rest on the bottom of the reactor 68. Rotor 70 is rotated at a speed for example of 2,000 rpm. The turbine blades 72 impel the gaseous material downwardly through reactor 68. The turbine blades 74 impel the gaseous material upwardly through reactor 68. Rotor 70 impels the gaseous material laterally into contact with catalyst bed 78. Gaseous effluent containing unreacted methane and oxygen and reaction products including methanol is withdrawn from reactor 68 through line 80. A bypass line 82 withdraws gaseous material from open reaction zone 66. Effluent from line 80 and gaseous material from line 82 maybe combined and passed through a condenser similarly to FIG. 1.

The following examples illustrate the invention:

EXAMPLE 1

A silicoferrate, iron sodalite, was synthesized by a modification of the method of Szostak and Thomas supra. A solution of 500 g. sodium silicate solution (Fisher Scientific) and 108 g. sodium hydroxide in 200 g. deionized water was prepared and designated solution A. A second solution, solution B, was prepared by adding 82 g. of 98% sulfuric acid and 80.4 g. of iron (III) nitrate nonahydrate (Aldrich) to 200 g. deionized water with stirring. Solution A and solution B were mixed by alternate addition of small aliquots of each to a beaker fitted with an overhead stirrer. Solution C was prepared by adding 82.7% tetramethylammonium chloride (Aldrich) to 137 g. deionized water.

Solution C was then rapidly added to the mixture of A and B with vigorous stirring. The resulting tan slurry had a relative molar composition ratio of 1.0 $Fe_2O_3$: 24.2 $SiO_2$: 20.7 $Na_2O$: 7.6 TMACl: 465 $H_2O$ and a pH of 11.5. The slurry was stirred without additional cooling for 15 minutes then charged to a Teflon lined 2 liter autoclave, sealed, and purged with argon. The reactor was pressurized to 200 psig with argon and allowed to crystallize with stirring at 168°-172° C. for 68 hours. The reactor product was washed with 1 liter of hot distilled water and 3 liters of room temperature distilled water and dried for 2 days at 125° C. in air. The recovered dried product (80.3 g.) was then calcined in an ebullating bed reactor under argon at 540° C. for one hour and in air at 540° C. for two hours. Chemical analysis indicated 10.6% by weight iron, and BET surface area measurement indicated 2.9 $m^2g^{-1}$. A portion of the calcined product (46 g.) was inpregnated with a binder consisting of 17 g. sodium silicate solution (Fisher Scientific) in 75 ml of water, dried at 125° C. overnight, ground and sized to 18/35 mesh, and calcined in a tube furnace exposed to air at 550° C. for one hour.

Chemical analysis indicated that the sample contained 10.11% Fe, 30.23% Si, 0.007% $SO_4^{2-}$, 0.018% Cl, and 4.03% Na, by weight, somewhat higher than the expected percentage of iron after dilution with the binder, which was 9.5%.

Given in Table 1 is a list of the major peaks obtained in the x-ray diffraction pattern of the above calcined sample prior to addition of binder, using CuK radiation and a solid state detector. The diffraction pattern of hydroxysodalite is given for reference. A small amount of a cancrinite phase may be present in the calcined sample.

TABLE I

| Calcined Sample | | Hydroxysodalite (hydrated, synthetic) | |
|---|---|---|---|
| 2-Theta | Relative Intensity | 2-Theta | Relative Intensity |
| 14.05 | 100 | 34.92 | 100 |
| 24.24 | 84 | 24.54 | 90 |

TABLE I-continued

| Calcined Sample | | Hydroxysodalite (hydrated, synthetic) | |
|---|---|---|---|
| 2-Theta | Relative Intensity | 2-Theta | Relative Intensity |
| 24.46 | 53 | 24.46 | 89 |
| 19.78 | 37 | 24.49 | 88 |
| 34.49 | 17 | 14.08 | 49 |
| 31.47 | 11 | 31.89 | 27 |
| 69.17 | 10 | 43.02 | 23 |
| 11.13 | 10 | 43.08 | 22 |
| 31.79 | 8 | 58.7 | 10 |
| 31.24 | 8 | | |
| 51.88 | 7 | | |
| 11.60 | 7 | | |
| 27.47 | 6 | | |
| 34.65 | 6 | | |
| 20.21 | 5 | | |
| 20.32 | 5 | | |
| 52.39 | 5 | | |
| 40.17 | 5 | | |
| 17.06 | 5 | | |
| 13.42 | 5 | | |
| 61.76 | 4 | | |
| 58.52 | 4 | | |
| 43.12 | 4 | | |

The catalyst thus prepared was used in the vapor-phase oxidation of methane to methanol as follows:

The catalyst was loaded into a glass-lined stainless steel reactor immersed in a sand bath heater and a 3/1 methane/air mixture was passed through the reactor at flow rates from 35 to 800 ml/min at room temperature and atmospheric pressure. 4 cc of 18-35 mesh catalyst were used. Water entered the system near the exit port of the reactor at a rate of 15 cc/min. The water captured the methanol in a knock-out vessel and after passage through a back-pressure regulator the gases were passed through a wet test meter into a gas buret which was sampled hourly. The aqueous methanol was analyzed by gas chromatography and the effluent gases were analyzed by both gas chromatography and mass spectrometry. Downstream traps showed that at least 95% of the methanol was captured in the water solution.

In the runs shown in Table 1, methane was oxidized to methanol in a plurality of runs over a solid granular catalyst in a quartz-lined tubular reactor, a portion of the gas at the head of the reactor bed could be drawn off instead of passing through the entire packed bed, as shown in FIG. 1. This slip stream is controlled by a needle valve and can be either trapped or recombined with the main flow exiting the bottom of the catalyst bed prior to the liquid condenser. In some of the runs, the bypass line 28 was closed, in others it was open. Ins some of the runs with the bypass line 28 open, trap 48 was in the flow path; these runs are identified in Table I as "trap". In other runs with the bypass open, trap 48 was not open. In some runs, the line 28 was taken off from a location six inches above the top of the catalyst bed 23. In other runs, identified in Table 1 as "take-off low" the line 78 was taken off from a location two inches above the top of the catalyst bed 23.

The conditions used and the results obtained are given in Table 2, for nine runs at the temperatures (Ti), gas hourly space velocity ("GHSV") indicated. The product rates in millimoles per hour for methanol, carbon monoxide and carbon dioxide, the millimoles of oxygen used and the percent selectivities and conversions are given for the respective runs. In runs wherein the trap 48 was in the flow path, the rates of methanol withdrawn through line 26 ("bed") and withdrawn by trap 48 ("trap") are given separately, along with the total for both ("tot"). It is believed that the trapping was more efficient in run 8 than in run 7 because of some changes in trap configuration.

TABLE 2

| RUN | $Ti.^2$ °C. | GHSV, $hr^{-1}$ | Methane Oxidations PRODUCTS, MMoles/hr | | | $O_2$ used MMoles | SEL,[3] % | Conv., % |
|---|---|---|---|---|---|---|---|---|
| | | | $CH_3OH$ | CO | $CO_2$ | | | |
| 1 By-Pass Closed[4] | 425 | 525 | 1.6 | 1.6 | 0.4 | 3.8 | 44 | 4.8 |
| 2 By-Pass Open[5] | 426 | 510 | 3.5 | 0.6 | 0.7 | 4.0 | 72 | 6.5 |
| 3 By-Pass Open Trap Insert[6] | 429 | 600 | 2.04 (BED) 1.60 (TRAP)[7] 3.64 (TOT)[8] | 1.0 | 0.5 | 4.3 | 71 | 6.0 |
| 4 By-Pass Open Trap Insert Take-Off Low[9] | 426 | 555 | 1.27 (BED) 2.51 (TRAP) 3.78 (TOT) | 1.1 | 0.7 | 5.0 | 68 | 7.0 |
| 5 By-Pass Closed | 437 | 1,305 | 3.3 | 5.7 | 1.4 | 11.7 | 31 | 5.6 |
| 6 By-Pass Open | 439 | 1,275 | 5.7 | 2.3 | 2.5 | 10.2 | 54 | 5.8 |
| 7 By-Pass Open Trap Insert[6] | 439 | 1,305 | 3.75 (BED) 2.02 (TRAP) 5.77 (TOT) | 2.1 | 2.1 | 10.5 | 58 | 5.4 |
| 8 By-Pass Open Trap Insert[6] | 431 | 1,215 | 2.80 (BED) 3.90 (TRAP) 6.70 (TOT) | 2.8 | 1.5 | 10.2 | 60 | 6.3 |
| 9 By-Pass Open Trap Insert Take-Off Low[9] | 427 | 1,275 | 1.74 (BED) 4.27 (TRAP) 6.01 (TOT) | 2.3 | 1.8 | 9.8 | 59 | 5.6 |

[1] A 3/1 methane/air mix at 800 psig passed over 4 cc Fe-Sodalite
[2] Temperature at center of Catalyst Bed
[3] $[CH_3OH / (CH_3OH + CO + CO_2)] \times 100$
[4] A take-off arm 6" above Catalyst Bed is connected to a valve which allows methanol which distills to exit without passing through the Catalyst Bed. If the by-pass valve is closed, no methanol can appear in the product that hasn't passed through the bed.
[5] If the by-pass valve is opened, methanol taken overhead goes directly to producer collection device.
[6] A trap is inserted in the take-off arm to collect methanol which distills overhead.
[7] Methanol collected in the trap
[8] Methanol in trap + methanol through bed.
[9] Take off arm dropped from 6" to 2" above bed.

The invention claimed is:
1. An oxidation process for converting feedstock to oxidation product comprising passing feedstock com- prising gaseous hydrocarbon or oxygenated hydrocarbon having 1 to 10 carbon atoms at a temperature of about 300° to 600° C. with air or oxygen through a reaction zone containing an open space and a bed of solid granular catalyst containing crystalline silicometallates having iron incorporated into the structural framework withdrawing oxidation product from said open space, and simultaneously withdrawing oxidation product from an additional location in the reaction zone representative of a longer contact with said catalyst bed than the products withdrawn from said open space.

2. Process according to claim 1 wherein said open space is above said catalyst bed and said other location is at or below the bottom of said catalyst bed.

3. Process according to claim 1 wherein at least a portion of said catalyst bed is dispersed beside at least a portion of said open space said first-mentioned withdrawing is from an upper portion of said open space, and said additional location is a lower portion of said open space.

4. Process according to claim 1 wherein said open space is 0.5 to 10 times the catalyst bed volume.

5. Process according to claim 1 wherein the average temperature of said open space is different than the average temperature of the catalyst bed.

6. Process according to claim 1 wherein a temperature gradient exists within the open space.

7. Process according to claim 1 wherein the reaction zone is adiabatic.

8. Process according to claim 1 wherein the feedstock is natural gas.

9. An oxidation process for converting feedstock to intermediate products and then to final oxidation products comprising passing a gaseous hydrocarbon or oxygenated hydrocarbon having 1-10 carbon atoms in gas phrase at a temperature of about 300° to 600° C. with air or oxygen through a reaction zone containing solid catalyst of crystalline silicometallates having iron incorporated into the structural framework withdrawing a mixture of intermediate and final oxidation products from the reaction zone, passing said mixture into an effluent zone free of catalyst, and introducing additional feedstock into the effluent zone to react noncatalytically with intermediate product in the mixture and to form additional final product.

* * * * *